United States Patent [19]

Otoi et al.

[11] 4,325,741

[45] Apr. 20, 1982

[54] FIBROIN-COATED PIGMENT AND PROCESSES FOR PRODUCING SAME

[75] Inventors: Kiyoshi Otoi, Nagano; Toshihiro Nasuno, Odawara, both of Japan

[73] Assignee: Kanebo, Ltd., Tokyo, Japan

[21] Appl. No.: 187,899

[22] Filed: Sep. 17, 1980

[30] Foreign Application Priority Data

Sep. 20, 1979 [JP] Japan ................................ 54-121121

[51] Int. Cl.$^3$ ........................ C04B 31/40; C08J 7/18; C09C 3/00
[52] U.S. Cl. ............................. 106/308 N; 106/308 P; 106/309
[58] Field of Search ........... 106/308 Q, 308 N, 308 P, 106/309; 424/31, 36, 63, 69, 359

[56] References Cited

U.S. PATENT DOCUMENTS

| | | | |
|---|---|---|---|
| 2,341,759 | 2/1944 | Catlin | 106/308 N |
| 3,160,600 | 12/1964 | Holsten et al. | 106/308 N |
| 3,753,922 | 8/1973 | Shimosaka et al. | 424/36 X |
| 3,927,199 | 12/1975 | Micchelli et al. | 424/359 X |
| 4,233,212 | 11/1980 | Otoi et al. | 424/63 X |

*Primary Examiner*—Carl F. Dees
*Attorney, Agent, or Firm*—Blanchard, Flynn, Thiel, Boutell & Tanis

[57] ABSTRACT

A fibroin-coated pigment and two processes for producing the same are disclosed. The fibroin-coated pigment comprises a carrier pigment in the form of finely divided particles whose surfaces are substantially coated with a film of regenerated fibroin and is characterized in that at least 50% by weight of the regenerated fibroin is constituted of hot-water-insoluble fibroin having the $\beta$-configuration.

21 Claims, No Drawings

FIBROIN-COATED PIGMENT AND PROCESSES FOR PRODUCING SAME

BACKGROUND OF THE INVENTION

This invention relates to a fibroin-coated pigment comprising a carrier pigment in the form of finely divided particles whose surfaces are substantially coated with a film of silk fibroin coagulated and precipitated from a solution thereof (hereinafter referred to as a film of regenerated fibroin) and having great utility in the manufacture of cosmetic preparations, coating compositions and the like, and to processes for producing the same.

Conventionally, pigments for use in cosmetic preparations and coating compositions have several disadvantages. That is, when dispersed in water, such pigments are liable to aggregation and precipitation, and when dispersed in oil, their oil absorption properties are suppressed to such an extent that they are hardly wetted with oil, cannot be dispersed therein satisfactorily, and hence are apt to aggregate. Especially in the case of cosmetic preparations, such pigments remove moisture and grease from the skin and bring about a dehydrated, degreased or dried condition which may roughen the skin. Moreover, they lack adhesion to the skin, spreadability on the skin, smoothness and the like. Thus, the direct use of such pigments can hardly produce satisfactory cosmetic effects. Furthermore, it is said that, when calcium carbonate and the like adsorb moisture thereon, the pH of the skin surface becomes alkaline and tends to roughen the skin.

In order to improve the properties of such pigments, a process for the production of a pigment having a silk-vinyl coating is disclosed in Japanese Patent Publication No. 250/'53. According to this process, a pigment (such as titanium oxide, zinc oxide, kaolin, talc, etc.) is mixed with a methanolic solution of polyvinyl acetate. While the resulting mixture is being stirred, a caustic potash solution containing fibroin is added thereto drop by drop to form and precipitate polyvinyl alcohol by the saponification of the polyvinyl acetate and, at the same time, to coagulate the fibroin by the action of the methanol. The white gelatinous precipitate so formed is heat-treated at 95° C. in the water-methanol-caustic potash system, allowed to cool, separated from the liquid phase, neutralized with hydrochloric acid, washed with alcohol and water, and then dried under reduced pressure.

However, the coated pigment obtained by this process has a coating composed of polyvinyl alcohol and fibroin. Though heat-treated (or crystalized), the polyvinyl alcohol tends to swell and dissolve in water. Accordingly, when water-base paints and cosmetics (such as face-powder fluid, cream and lotion) containing this coated pigment are stored for a long period of time, the polyvinyl alcohol may swell or dissolve. Moreover, when this coated pigment is dyed, the polyvinyl alcohol may dissolve in the dyeing solution and cause the surfaces of the pigment particles to be exposed partially. In consequence, the resulting coated pigment lacks in dispersibility in water and evenness of dyeability, and the final products (e.g., cosmetic preparations) containing it are poor in such properties as adhesion, spreadability, storage stability, etc. Furthermore, the fibroin present in the coating is denatured and hardened to a considerable degree because of the use of alkali in the production process and the heat treatment in the presence thereof, and it is not intimately mixed with the hard polyvinyl alcohol. Accordingly, the coating is apt to break as a result of intensive blending during the manufacture of coating compositions and cosmetic preparations (such as face powder and cheek rouge) in powder form. Moreover, this coated pigment is poor in such properties as feeling, adhesion to the skin, spreadability on the skin, oil absorption, dispersibility in oil, color fastness, etc., and is liable to undergo peeling-off of the coating and bleeding of the dye under the influence of water or sweat. In addition, the above-described process involves the use of large amounts of strong alkali (which is apt to denature fibroin) and methanol (which is toxic and dangerous) and requires a considerable number of troublesome operations, which makes it difficult to put this process into practice on an industrial scale.

In Japanese Patent Publication No. 299/'52, a formulation for the production of a face powder is described as Example 4. According to this formulation, a portion of 1.385 g of a pigment is intimately mixed with 5.0 g of a colloidal solution of fibroin (as a binder). Then, the remainder of the pigment and an appropriate amount of coloring matter are added to and blended with the resulting mixture. Finally, 35 g of perfume is incorporated therein to obtain a face powder.

However, it is well known that, when such a small amount of binder (i.e., a colloidal solution of fibroin) is mixed with a large amount of pigment, the binder is only partially deposited on the surface of the pigment particles, and not over the entire surfaces of the pigment particles. Even if the pigment having the binder deposited thereon is dried (in air or by heating), the structure in which the surfaces of the pigment particles are uniformly coated with a film of fibroin is not created and, moreover, the fibroin is scarcely converted into that type of fibroin having the $\beta$-configuration. Accordingly, this fibroin-loaded pigment and the face powder containing it are insufficient in such properties as adhesion to the skin, spreadability on the skin, and oil absorption, and the fibroin present on the surfaces of the pigment particles tends to cohere or peel off under the influence of water or sweat. Thus, they can hardly produce good cosmetic effects.

In addition, silk powder (consisting of fibroin alone) has been used in cosmetic preparations in powder form, because of its silk-like feeling, good gloss, high ultraviolet-absorbing powder, moderate hydrophilic-lipophilic balance, good adhesion to the skin, and the like.

However, silk powders produced by conventional grinding techniques, silk powders in granular form, and the like do not permit microscopically intimate mixing. Moreover, in order that the covering power and gloss of the pigment (e.g., talc, titanium oxide, mica, etc.) may be retained to a full extent, they must be used in an amount of no more than several percent. Accordingly, it is impossible to make good use of the excellent properties possessed inherently by fibroin. In order to utilize the properties of fibroin, the use of a microscopically intimate mixture in which the surfaces of finely divided particles of a pigment are masked (or coated) with fibroin particles is ideal. However, this is utterly infeasible in view of the particle shape and particle size of conventional silk powders.

BRIEF SUMMARY OF THE INVENTION

The above-described disadvantages of the prior art can be wholly overcome by this invention. Thus, it is an object of this invention to provide a fibroin-coated pigment which is very excellent in such properties as adhesion, spreadability, dispersibility, compatibility, covering power, oil absorption, hydrophilic-lipophilic balance, the ability to prevent the formation of oil droplets, feeling, skin-protecting ability, dyeability, coating stability, etc. and which is very useful in the manufacture of cosmetic preparations, coating compositions and the like. Another object of this invention is to provide processes for producing such a fibroin-coated pigment with industrial advantages.

In accordance with one aspect of this invention, there is provided a fibroin-coated pigment comprising a carrier pigment in the form of finely divided particles whose surfaces are substantially coated with a film of regenerated fibroin, characterized in that at least 50% by weight of the regenerated fibroin is constituted of hot-water-insoluble fibroin having the $\beta$-configuration.

In accordance with another aspect of this invention, there is provided a process for producing a fibroin-coated pigment which comprises the steps of dissolving a degummed silk material in at least one solvent selected from the group consisting of an aqueous cupri-ethylenediamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc, and an aqueous sodium solution; dispersing a carrier pigment in the resulting fibroin solution having a fibroin concentration of from 3 to 20% by weight; adding a coagulating salt to the pigment-loaded fibroin solution to coagulate and precipitate (or regenerate) the fibroin; dehydrating and drying the resulting coagulum; and then pulverizing the dried product.

In accordance with still another aspect of this invention, there is provided a process for producing a fibroin-coated pigment which comprises the steps of dissolving a degummed silk material in at least one solvent selected from the group consisting of an aqueous cupri-ethylenediamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc, and an aqueous sodium thiocyanate solution; dialyzing the resulting fibroin solution; dispersing a carrier pigment in the resulting aqueous fibroin solution having a fibroin concentration of from 3 to 20% by weight; subjecting the pigment-loaded aqueous fibroin solution to at least one treatment for coagulating and precipitating (or regenerating) the fibroin, the treatment being selected from the group consisting of the addition of a coagulating salt, aeration, coagulation at the isoelectric point, exposure to ultrasonic waves, and agitation at high shear rate; dehydrating and drying the resulting coagulum; and then pulverizing the dried product.

DETAILED DESCRIPTION OF THE PREFERRED EMBODIMENTS

The fibroin-coated pigment of this invention comprises a carrier pigment in the form of finely divided particles whose surfaces are substantially coated with a film of regenerated fibroin, and the film of regenerated fibroin usually forms a substantially uniform coating on the pigment particles. In addition, it is characterized by the fact that at least 50% by weight, preferably from 80 to 100% by weight, and most preferably from 90 to 100% by weight of the regenerated fibroin is constituted of hot-water-insoluble fibroin having the $\beta$-configuration. If the hot-water-insoluble fibroin content is less than 50% by weight, the fibroin becomes extremely hydrophilic. As a result, the fibroin-coated pigment undergo agglomeration or cohesion under the influence of water or sweat to form secondary particles (i.e., they gather together to form coarse particles). Moreover, the film is apt to peel off when the dispersion medium is water (e.g., in the case of water-base paints and cosmetics), and the dispersibility is apt to decrease when the dispersion medium is oil (e.g., in the case of oil-base paints and cosmetics). Furthermore, when applied to the skin, the fibroin-coated pigment is poor in such properties as spreadability, feeling, etc.

The term "hot-water-insoluble fibroin" as used herein means that type of fibroin which cannot be dissolved by boiling it in hot water at 100° C. for 15 minutes. This hot-water-insoluble fibroin is characterized by the fact that the hydrogen bonding between fibroin molecules represents essentially the $\beta$-configuration.

The film of regenerated fibroin generally has a degree of crystallinity of at least 10% and preferably from 20 to 43%, though it may vary slightly according to the conditions of the production process.

The degree of crystallinity of the film of regenerated fibroin present in the fibroin-coated pigment of this invention is generally lower than the degrees of crystallinity (ranging from about 50 to about 55%) of natural silk thread and degummed silk materials, and markedly higher than the degree of crystallinity of the films of regenerated fibroin obtained by prior art processes such as those described in Japanese Patent Publication Nos. 250/'53 and 299/'52. Moreover, the hot-water-insoluble fibroin content (or the rate of $\beta$-configuration) of regenerated fibroin present in the fibroin-coated pigment of this invention is much higher than the hot-water-insoluble fibroin contents of the regenerated fibroins obtained by the aforesaid prior art processes.

The film of regenerated fibroin is present in an amount of from 2 to 100% by weight and preferably from 5 to 50% by weight based on the weight of the carrier pigment. If the amount is less than 2% by weight, the desired structure in which the surfaces of finely divided particles of a carrier pigment is substantially coated with a film of regenerated fibroin cannot be created. Accordingly, it is difficult to endow the fibroin-coated pigment with satisfactorily good properties such as adhesion, spreadability, dispersibility, covering power, skin-protecting ability, feeling, etc. On the other hand, if the amount is greater than 100% by weight, the fibroin-coated pigment may tend to decrease in covering power.

The film of regenerated fibroin generally has a thickness of from 0.01 to 50$\mu$.

The regenerated fibroin present in the fibroin-coated pigment of this invention has an average molecular weight of not less than 50,000 and preferably from 80,000 to 150,000.

The fibroin-coated pigment of this invention has a maximum particle diameter of from 0.05 to 100$\mu$, preferably from 0.05 to 60$\mu$, and most preferably from 0.1 to 30$\mu$. If the maximum particle diameter is greater than 100$\mu$, the fibroin-coated pigment tends to become poor in such properties as adhesion to the skin, affinity for the skin, spreadability on the skin, etc.

The carrier pigment which is used in the fibroin-coated pigment of this invention can be any of the well-known pigments for use in cosmetic preparations and coating compositions, including white pigments, color pigments, extender pigments, pearlescent pigments and the like. Typical examples thereof are talc, kaolin, mica, calcium carbonate, titanium oxide, zinc oxide, micaceous titanium, magnesium carbonate, iron oxides, zinc stearate, magnesium stearate, magnesium silicate and organic pigments. These pigments may be used alone or in combination. The carrier pigment generally has a maximum particle diameter of from 0.03 to 100μ.

As stated before, the fibroin-coated pigment of this invention is characterized by the fact that the film of regenerated fibroin forms a substantially uniform coating on the pigment particles. Accordingly, the fibroin-coated pigment can be colored evenly, brightly and fadelessly with dyestuffs for silk such as acid dyes, metallized dyes, etc., and it can also be used effectively used as a colored pigment.

The manner in which the surface of finely divided particles of the carrier pigment is coated with the film of regenerated fibroin can be observed by dyeing the fibroin-coated pigment with Tartrazine NS (C.I. Acid Yellow 23) known as an acid dye or Shirlastain A (Imperial Chemical Industry Co., Ltd.) known as a dye for identification of silk, and then examining the evenly and brightly colored particles microscopically in comparison with uncoated and hence uncolored particles of the same pigment. More specifically, the fibroin-coated pigment of this invention is dyed in a bright yellow color with Tartrazine NS and in a dark brown color wth Shirlastain A, while the carrier pigment is not dyed at all.

Also as stated before, the fibroin-coated pigment of this invention has the structure in which the surfaces of finely divided particles of a carrier pigment are substantially coated with a film of regenerated fibroin, and takes the form of a fine powder. Accordingly, the fibroin-coated pigment per se is markedly excellent in such properties as adhesion to the skin, spreadability, feeling, moisture retention, buffer capacity, covering power, hydrophilic-lipophilic balance, skin-protecting ability, etc. Thus, the fibroin-coated pigment of this invention can overcome the disadvantages of conventional pigments, i.e., the problems of dehydration, degreasing or drying of the skin, of alkalification of the skin surface, and the like, and can keep the skin intact.

In addition, the film of regenerated fibroin has a high rate of $\beta$-configuration because at least 50% by weight of the regenerated fibroin is constituted of hot-water-insoluble fibroin having the $\beta$-configuration, and has a moderate degree of molecular orientation. Accordingly, when used in water-base or oil-base coating compositions and cosmetic preparations, the fibroin-coated pigment of this invention is also markedly excellent in such properties as the uniformity of dispersion, the ability to prevent the formation of oil droplets, stability, compatibility with inorganic powder materials, color fastness, the ability to control the moisture content of the skin, etc. Thus, the fibroin-coated pigment of this invention does not present the above-described phenomena, such as agglomeration or cohesion, the formation of secondary particles, peeling-off of the coating, etc., under the influence of water or sweat.

As described above, the fibroin-coated pigment of this invention has great utility in the manufacture of cosmetic preparations and coating compositions, and can thereby produce beneficial cosmetic and coating effects.

In accordance with this invention, the fibroin-coated pigment having the aforesaid meritorious features can be produced by either of the above-described two processes.

The solvent for fibroin which is used in the practice of this invention can be an aqueous cupri-ethylenediamine solution, an aqueous ammoniacal solution of cupric hydroxide (Schweitzer's reagent), an aqueous alkaline solution of cupric hydroxide and glycerol (Roe's reagent), an aqueous lithium bromide solution, an aqueous solution of the chloride, nitrate or thiocyanate of calcium, magnesium or zinc, or an aqueous sodium thiocyanate solution. However, it is preferable to use an aqueous solution of the chloride or nitrate of calcium or magnesium, because of its low cost and convenience for use. The concentration of these solutions may vary according to the type of solute used, temperature and the like. Where an aqueous solution of a metal salt is used, its concentration is generally from 10 to 80% by weight, preferably from 20 to 70% by weight, and most preferably from 25 to 60% by weight.

The silk material which is used in the practice of this invention can be cocoons, raw silk, waste cocoons, raw silk waste, bisu, unreelable cocoons, silk fabric waste, bourette or the like. Prior to use, the silk material is degummed or freed from sericin by any conventional procedure. This can be done, for example, by washing the silk material in warm water containing a surface-active agent or an enzyme, as required, and then drying it.

The fibroin solution which is used in the practice of this invention is a solution obtained by dissolving an appropriate amount of the degummed silk material in the above-defined solvent for fibroin. More specifically, employing a suitable apparatus such as kneader, the degummed silk material is added to the solvent and made into a homogeneous solution at a temperature of from 60° to 95° C. and preferably from 70° to 85° C. Where the coagulation step is to be carried out by the addition of a coagulating salt (according to the first process of this invention), the resulting fibroin solution may be used directly, that is, without subjecting it to dialysis. However, where the coagulation step is to be carried out by other means (according to the second process of this invention), the fibroin solution must be dialyzed prior to use. It is more preferable to dialyze the fibroin solution in case of the addition of a coagulating salt.

In the dialysis step, it is desirable to remove the salt and other contaminants almost completely by means of a dialyzer using semipermeable membranes or hollow fibers, typically made of cellulose acetate. In order that a stabler gel of fibroin may be rapidly formed on the surfaces of finely divided particles of the carrier pigment, there must be a proper correlation between the volume of the fibroin solution to be dialyzed and the surface area of the dialysis membrane. More specifically, the dialysis step should desirably be carried out by the use of a multilayer membrane structure or bundled hollow-fiber structure satisfying the condition expressed by $$\frac{\text{Membrane Surface Area (cm}^2)}{\text{Priming Volume (cm}^3)} \geq 10$$

where the priming volume means the internal volume within the dialysis tubes or between the layers of dialysis membrane. The above-defined ratio preferably has a value of not less than 30 and most preferably a value of not less than 50.

In order to satisfy the aforesaid condition, it is necessary to keep the spacing between the layers of dialysis membrane at 2 mm or less in the case of a multilayer membrane structure or to keep the diameter of hollow fibers at 4 mm or less in the case of a bundled hollow-fiber structure. The aqueous fibroin solution resulting from this dialysis step has a very low residual salt concentration of from 0.03 to 0.06% by weight, so that the purity of fibroin can preferably be maintained at a high level.

The aqueous fibroin solution resulting from the dialysis step is adjusted, either by concentration or by dilution, to a predetermined fibroin concentration.

The fibroin solution or aqueous fibroin solution which is used in the practice of this invention should have a fibroin concentration of from 3 to 20% by weight, preferably from 4 to 15% by weight, and most preferably from 5 to 10% by weight. If the fibroin concentration is less than 3% by weight, an uneconomically long time is required for the coagulation of the fibroin solution or aqueous fibroin solution and a uniform gel of fibroin is not formed on the surfaces of finely divided particles of the carrier pigment. On the other hand, if the fibroin concentration is greater than 20% by weight, it may be difficult to dehydrate the resulting coagulum in a subsequent dehydration step. Furthermore, if the fibroin concentration is outside the aforesaid range, the resulting film of regenerated fibroin may be low in hot-water-insoluble fibroin content (or the rate of $\beta$-configuration) and, therefore, the resulting fibroin-coated pigment tends to agglomerate, form secondary particles, or undergo peeling-off of the coating under the influence of sweat or water used as a dispersion medium.

While a required amount of the fibroin solution or aqueous fibroin solution is being stirred, the above-defined carrier pigment is added thereto and dispersed therein to form a homogeneous suspension. Then, this suspension is subjected to a coagulation step.

The amount of fibroin solution or aqueous fibroin solution used may vary according to the fibroin concentration thereof, the amount of regenerated fibroin desired, and the like. However, the fibroin solution or aqueous fibroin solution is generally used in an amount of not less than 100% by weight, preferably not less than 300% by weight, and most preferably from 500 to 1,000% by weight based on the weight of the carrier pigment. If the amount is less than 100% by weight, the film of regenerated fibroin is only partially deposited on the surfaces of the pigment particles and is incapable of coating them to a substantial degree. Accordingly, the resulting fibroin-coated pigment is hardly endowed with satisfactorily good properties such as adhesion to the skin, spreadability, covering power, evenness of dyeability, skin-protecting ability, dispersibility, hydrophilic-lipophilic balance, etc. Generally speaking, larger amounts of the fibroin solution or aqueous fibroin solution produce better results. However, the use of too large amounts of the fibroin solution or aqueous fibroin solution uneconomically increases the required amount of a coagulating agent and the like.

As stated before, the coagulation step for the pigment-loaded fibroin solution is carried out by the addition of a coagulating salt. In case of the pigment-loaded aqueous fibroin solution, however, the coagulation step is carried out by subjecting it to a treatment selected from the group consisting of the addition of a coagulating salt, aeration, coagulation at the isoelectric point, exposure to ultrasonic waves, agitation at high shear rate, and combinations thereof.

The coagulating salt can be any salt that coagulates the fibroin present in the pigment-loaded fibroin solution or aqueous fibroin solution. Typical examples thereof are sodium chloride, potassium chloride, sodium sulfate, potassium sulfate, ammonium sulfate, sodium nitrate, potassium nitrate and the like. The coagulating salt may be added as such or in the form of an aqueous solution. The coagulating salt is used in an amount of from 2 to 10% by weight based on the weight of the water present in the coagulation system.

Aeration is carried out by bubbling air through the pigment-loaded aqueous fibroin solution according to any suitable technique. For each liter of the pigment-loaded aqueous fibroin solution, air is generally fed at a rate of at least 0.1 l/min. The aeration time is generally 10 minutes or more, though it may vary according to the feed rate of air.

Coagulation at the isoelectric point is carried out by adding an inorganic acid (such as hydrochloric acid, sulfuric acid, etc.) or an organic acid (such as acetic acid, citric acid, etc.), with stirring, to the pigment-loaded aqueous fibroin solution until its pH reaches 4.5. Then, this pigment-loaded aqueous fibroin solution is usually allowed to stand at room temperature for a period of 10 minutes or more.

Exposure to ultrasonic waves is carried out by placing the pigment-loaded aqueous fibroin solution in an ultrasonic wave generator and exposing it, with stirring, to ultrasonic waves which generally have a frequency of 30 kHz or more. The fibroin is coagulated by continuing this treatment at room temperature for a period of 1 hour or more.

The fibroin can also be coagulated and precipitated simply by agitating the pigment-loaded aqueous fibroin solution. However, this agitation must be carried out at a high shear rate which is generally 50/sec or more and preferably 100/sec or more. The agitation time required for gelation is generally 1 hour or more, though it may vary according to the fibroin concentration of the aqueous fibroin solution, the shear rate employed, and the like.

During this agitation at high shear rate, methyl alcohol, ethyl alcohol, isopropyl alcohol or acetone may be added to the pigment-loaded aqueous fibroin solution in order to increase the rate of $\beta$-configuration of the regenerated fibroin to 90% or more. The amount of alcohol or acetone added is suitably from 1 to 100% by weight based on the weight of the pigment-loaded aqueous fibroin solution. However, the addition of such a water-soluble organic solvent is not a requisite for this invention.

After the pigment-loaded fibroin solution or aqueous fibroin solution has been subjected to one or more of the above-described treatments for coagulating the fibroin, the resulting coagulum (consisting of the carrier pigment coated with a gel of regenerated fibroin) is dehydrated for the purpose of separating it from the liquid phase (consisting of water and other components). This dehydration step is preferably carried out by the use of a centrifuge, and the gel of regenerated fibroin present on the surfaces of the pigment particles is generally dehydrated to a water content of the order of from 100 to 500% by weight based on its dry weight. The dehydrated coagulum can then be easily dried to the absolute dry state. This drying step is carried out at a temperature of from 60° to 120° C. under normal or reduced pressure.

The dried product (consisting of aggregates of the pigment particles coated with a film of regenerated fibroin) is easily pulverized by the use of a pulverizer such as hammer mill, jet mill, etc. The particle size should generally be adjusted to a maximum particle diameter of from 0.05 to 100μ, preferably from 0.05 to 60μ, and most preferably from 0.1 to 30μ.

The resulting fibroin-coated pigment, which is characterized by the fact that at least 50% by weight of the regenerated fibroin is constituted of hot-water-insoluble fibroin, is excellent in such properties as hydrophilic-lipophilic balance, the ability to prevent the formation of oil droplets, moisture retention, water resistance, dispersibility in water or oil, etc. and is scarcely liable to the formation of secondary particles, cohesion, excessive swelling and the like under the influence of water or sweat. However, the regenerated fibroin can further be insolubilized in hot water (i.e., its hot-water-insoluble fibroin content or rate of β-configuration can further be enhanced) and, therefore, the aforesaid properties thereof can further be improved by the application of a wet heat treatment as described below.

The wet heat treatment can be carried out according to either of the following two procedures. That is, the product resulting from the drying or pulverizing step may be heat-treated with saturated steam at a temperature of 50° C. or above and preferably from 80° to 120° C. alternatively, prior to the drying step, the coagulum may be heat-treated at a temperature of 50° C. or above in an aqueous solution of a neutral salt such as sodium chloride potassium chloride, sodium sulfate, potassium sulfate, ammonium sulfate, sodium nitrate, etc. or in an organic solvent such as acetone, alcohol, etc. By the application of this wet heat treatment, not only the regenerated fibroin can further be insolubilized in hot water (i.e., its rate of β-configuration can further be enhanced) as described above, but also its degree of crystallinity can further be increased, so that the resulting fibroin-coated pigment is likely to be excellent in such properties as hydrophilic-lipophilic balance, the ability to prevent the formation of oil droplets, dispersibility in various dispersion media, coating stability, color fastness, etc.

This invention is further illustrated by the following examples. In these examples, parts and percentages are by weight, except for the percentages representing degrees of crystallinity.

With respect to the fibroin-coated pigments obtained in these examples, the amount (%) of regenerated fibroin present on the pigment particles, the hot-water-insoluble fibroin content (%) of the regenerated fibroin, and the degree of crystallinity (%) of the film of regenerated fibroin were determined according to the following procedures.

1. Amount (%) of Regenerated Fibroin Present on Pigment Particles

The nitrogen content (%) of a sample (of a fibroin-coated pigment to be tested) is determined by the Kjeldahl method [J. Kjeldahl: Z. anal. Chem., 22, 366 (1883)]. From this nitrogen content, the regenerated fibroin content (%) of the sample is calculated according to the following equation:

Regenerated Fibroin Content (%) of Sample = Nitrogen Content (%) × (100/16)

Then, this regenerated fibroin content of the sample is converted into the amount (%) of regenerated fibroin present on the pigment particles.

2. Hot-water-insoluble Fibroin Content (%) of Regenerated Fibroin

A 10-g sample (absolute dry weight) of a fibroin-coated pigment to be tested is boiled in 1 l of hot water at a temperature of 100° C. for a period of 15 minutes, and the absolute dry weight of the undissolved portion of the sample is measured. Thus, the weight of the dissolved fraction of the regenerated fibroin is determined. Then, the hot-water-insoluble fibroin content (%) is calculated according to the following equation:

$$\text{Hot-water-insoluble Fibroin Content (\%)} = \left(1 - \frac{w}{W}\right) \times 100$$

where W stands for the weight of the regenerated fibroin present in the sample and w for the weight of the dissolved fraction of the regenerated fibroin. If the carrier pigment is more or less soluble in hot water, it is boiled under the same conditions to determine its solubility, which is used to correct the weight of the dissolved fraction of the regenerated fibroin.

3. Degree of Crystallinity (%) of Film of Regenerated Fibroin

Employing the reflection method, the X-ray diffraction intensity curve of a sample powder is automatically recorded over an angle range of $2\delta = 10°-35°$ C. Then, the fibroin intensity curve is derived by subtracting the diffraction peaks attributable to the carrier pigment from the above X-ray diffraction intensity curve. The area under this fibroin intensity curve is denoted by Xs. On the other hand, a reference powder containing amorphous fibroin and the carrier pigment in the same proportion as that of the sample powder is prepared, and the X-ray diffraction intensity curve thereof is obtained in the same manner as described above. The area under the similarly derived amorphous fibroin intensity curve is denoted by Xa. Then, the degree of crystallinity (%) is calculated according to the following equation:

$$\text{Degree of Crystallinity (\%)} = \frac{Xs - Xa}{Xa} \times 100$$

The amorphous fibroin is prepared by pouring a 5% (w/w) aqueous fibroin solution on a Teflon plate, drying it at a temperature of 50° C., and then grinding the resulting film at low temperatures.

EXAMPLE 1

Spun silk waste was used as the starting material for the production of a fibroin-coated pigment. One hundred parts of spun silk waste was added to a solution of 30 parts of marseille soap in 3,000 parts of water, stirred at 95°–98° C. for 3 hours to reduce its gum content to 0.1% or less, washed with water, and then dried in hot air at 80° C. An aqueous solution containing 8% of ethylenediamine and 6% of cupric hydroxide (i.e., a cupri-ethylenediamine solution) was prepared, and 10 parts of the spun silk waste degummed and dried as above was dissolved in 100 parts of the cupri-ethylenediamine solution by stirring at room temperature for 5 minutes. The resulting solution was immediately adjusted to pH 6.8 with 10% acetic acid and then diluted with water to prepare a 5% fibroin solution.

To 100 parts of this 5% fibroin solution was added 10 parts of talc having a maximum particle diameter (or major diameter) of 10–20μ. The resulting mixture was vigorously stirred at room temperature to form a homogeneous suspension. While this suspension was being vigorously stirred, 20 parts of a 30% aqueous solution of sodium sulfate was added thereto and mixed therewith to coagulate and precipitate (or regenerate) the fibroin on the surfaces of the talc particles. The coagulum so formed was separated by filtration, washed thoroughly with water until the washings no longer contained sulfate ions, dehydrated by centrifugation, and then dried at 105° C. The resulting product was pulverized in a hammer mill to obtain a fibroin-coated pigment having a particle diameter of 10–30μ. When this fibroin-coated pigment was dyed with a 2% aqueous solution of the acid dye Tartrazine NS and then examined under an optical microscope, the entire surfaces of the particles were found to be brightly and evenly colored in yellow. This demonstrates that the particles of the talc used as the carrier pigment were uniformly coated with a film of regenerated fibroin. (When talc alone was dyed under the same conditions, it was not colored at all.)

When determined according to the above-described procedures, the amount of regenerated fibroin present on the talc particles was 50.1% based on the weight of the talc, and the hot-water-insoluble fibroin content of the regenerated fibroin was 50.2% based on the weight of the regenerated fibroin. Moreover, the film of regenerated fibroin had a degree of crystallinity of 10.1%, while a powder of the degummed spun silk waste had a degree of crystallinity of 51%.

Then, the above fibroin-coated pigment (Test Run 1), talc having 3% of a conventional fibroin powder (or silk powder) blended therewith (Control Run 1), talc having 50.1% of the same fibroin powder blended therewith (Control Run 2), and talc alone (control Run 3) were subjected to practical performance tests for the purpose of evaluating their performance as a cosmetic preparation (e.g., face powder). These tests were conducted by a panel of 10 skilled examiners. The results thus obtained are summarized in Table 1.

TABLE 1

| Powder Sample | Moisture Retention | Adhesion to the Skin | Spreadability on the Skin | Oil Absorption | Feeling | Covering Power |
|---|---|---|---|---|---|---|
| Test Run 1 | ⊙ | ○ | ○ | ⊙ | ⊙ | ○ |
| Control Run 1 | Δ | Δ | ○ | Δ | ○ | ○ |
| Control Run 2 | ⊙ | ○ | X | ⊙ | X | X |
| Control Run 3 | X | X | Δ | X | ○ | ⊙ |

Note:
The above properties were rated as very good (⊙), good (○), somewhat poor (Δ) or poor (X)

Thus, the fibroin-coated pigment produced in accordance with this invention were very good or good in such properties as moisture retention, adhesion to the skin, spreadability on the skin, oil absorption and feeling, and proved to be very useful as a base material for cosmetic preparations such as face powder, etc.

EXAMPLE 2

Spun silk waste was degummed in the same manner as described in Example 1 and used as the starting material for the production of a fibroin-coated pigment. One hundred parts of a 50% aqueous solution of calcium chloride was prepared by dissolving 82 parts of calcium chloride ($CaCl_2.4H_2O$) in 18 parts of water, and then heated to 110° C. Thereafter, 10 parts of the degummed spun silk waste was added, with stirring, to the calcium chloride solution over a period of 5 minutes and dissolved therein completely by stirring for an additional 30 minutes. The resulting fibroin-calcium chloride solution was cooled and then desalted by dialysis. More specifically, the fibroin-calcium chloride solution was placed in a cellulose tube having an internal diameter of 7–8 cm and a length of 1 m, its both ends were sealed, and the tube was immersed in running water for 15–25 hours, whereby the salt concentration of the solution was reduced to 0.01% or less. After completion of the dialysis, the resulting aqueous fibroin solution had a fibroin concentration of 5.1%.

While 50 parts of this aqueous fibroin solution was being stirred, 10 parts of titanium oxide having a particle diameter of 0.1–10μ was added thereto and dispersed therein to form a homogeneous suspension. In order to coagulate and precipitate the fibroin (i.e., in order to effect gelation of the fibroin), this suspension was intensively agitated at room temperature by means of such an agitator as to give a shear rate of 100/sec. Initially, the coagulation system was in the form of an aqueous fibroin solution having titanium oxide suspended therein. In the course of 2–3 hours' agitation, the fibroin gradually coagulated and precipitated on the surfaces of the titanium oxide particles. Ultimately, the whole system formed a mass of gel. This mass of gel was dehydrated by means of a centrifuge and then dried at 105° C. Thereafter, the resulting product was pulverized in a jet mill until its particle diameter was reduced to 0.1–0.5μ, and then subjected to a wet heat treatment (for insolubilizing the regenerated fibroin in hot water) comprising exposure to saturated steam at 110° C. for 5 minutes. When the fibroin-coated pigment thus obtained was dyed in the same manner as described in Example 1 and then examined microscopically, the entire surfaces of the particles were found to be brightly and evenly colored in yellow. This demonstrates that the particles of the titanium oxide used as the carrier pigment were uniformly coated with a film of regenerated fibroin. (When the film of regenerated fibroin present on the titanium oxide particles was removed by dissolving it in the aforesaid solvent, and then dyed under the same conditions, the particles were not colored at all.)

When determined according to the above-described procedures, the amount of regenerated fibroin present on the titanium oxide particles was 25.2% based on the weight of the titanium oxide, and the hot-water-insoluble fibroin content of the regenerated fibroin was 88.4% based on the weight of the regenerated fibroin. Moreover, the film of regenerated fibroin had a degree of crystallinity of 27.0%.

Then, the above fibroin-coated pigment (Test Run 2), titanium oxide having 3% of a conventional fibroin powder blended therewith (Control Run 4), titanium oxide having 25.2% the same fibroin powder blended therewith (Control Run 5), and titanium oxide alone (Control Run 6) were subjected to practical performance tests for the purpose of evaluating their performance as a face powder. These tests were conducted in the same manner as described in Example 1. The results thus obtained are summarized in Table 2.

TABLE 2

| Powder Sample | Moisture Retention | Adhesion to the Skin | Spreadability on the Skin | Oil Absorption | Feeling | Covering Power |
|---|---|---|---|---|---|---|
| Test Run 2 | ◉ | ◉ | ◉ | ◉ | ◉ | ◉ |
| Control Run 4 | △ | X | O | △ | O | ◉ |
| Control Run 5 | O | O | X | O | △ | X |
| Control Run 6 | X | X | O | X | X | ◉ |

Note:
The above properties were rated as very good (◉), good (O), somewhat poor (△) or poor (X).

Thus, the fibroin-coated pigment produced in accordance with this invention was very good in such properties as moisture retention, adhesion to the skin, spreadability on the skin, oil absorption and feeling, and proved to be markedly excellent as compared with the blends of a conventional fibroin powder and the uncoated carrier pigment or with the uncoated carrier pigment alone.

EXAMPLE 3

Spun silk waste was degummed in the same manner as described in Example 1 and used as the starting material for the production of fibroin-coated pigments. A 50% aqueous solution of zinc chloride was prepared by dissolving anhydrous zinc chloride ($ZnCl_2$) in water, and then heated to 70° C. Employing the same procedure as described in Example 2, the degummed spun silk waste was added thereto and dissolved therein to prepare a fibroin-zinc chloride solution having a fibroin concentration of 10%. Thereafter, the procedure of Example 1 was repeated except that the above solution was used as the coating solution, calcium carbonate, mica or red iron oxide as the carrier pigment, and a 35% aqueous solution of ammonium sulfate as the coagulating agent. When the fibroin-coated pigments thus obtained were dyed in the same manner as described in Example 1, the entire surfaces of the particles were found to be brightly and evenly colored in yellow, as was the case with the fibroin-coated pigment of Example 1. This demonstrates that, in all of the above fibroin-coated pigments, the particles of the carrier pigment were coated with a film of regenerated fibroin in a substantially uniform manner.

For the fibroin-coated pigment using calcium carbonate as the carrier pigment (Test Run 3), the amount of regenerated fibroin was 98.8%, the hot-water-insoluble fibroin content was 68%, and the degree of crystallinity was 20%. For the fibroin-coated pigment using mica as the carrier pigment (Test Run 4), the amount of regenerated fibroin was 99.1%, the hot-water-insoluble fibroin content was 85.3%, and the degree of crystallinity was 15.3%. For the fibroin-coated pigment using red iron oxide as the carrier pigment (Test Run 5), the amount of regenerated fibroin was 98.2%, the hot-water-insoluble fibroin content was 92.1%, and the degree of crystallinity was 30.3%.

Then, the above fibroin-coated pigments (Test Runs 3, 4 and 5), calcium carbonate having 98.8% of a fibroin powder blended therewith (Control Run 7), calcium carbonate alone (Control Run 8), mica having 99.1% of a fibroin powder blended therewith (Control Run 9), mica alone (Control Run 10), red iron oxide having 98.2% of a fibroin powder blended therewith (Control Run 11), and red iron oxide alone (Control Run 12) were subjected to practical performance tests for the purpose of evaluating their performance as a cosmetic preparation (e.g., face powder). These tests were conducted in the same manner as described in Example 1. The results thus obtained are summarized in Table 3.

TABLE 3

| Powder Sample | Moisture Retention | Adhesion to the Skin | Spreadability on the Skin | Oil Absorption | Feeling | Covering Power |
|---|---|---|---|---|---|---|
| Test Run 3 | ◉ | ◉ | ◉ | ◉ | ◉ | O |
| Control Run 7 | ◉ | O | X | △ | O | X |
| Control Run 8 | X | X | O | X | △ | ◉ |
| Test Run 4 | ◉ | ◉ | ◉ | ◉ | ◉ | ◉ |
| Control Run 9 | ◉ | O | X | O | △ | X |
| Control Run 10 | X | X | ◉ | X | △ | O |
| Test Run 5 | ◉ | ◉ | ◉ | ◉ | ◉ | ◉ |
| Control Run 11 | ◉ | O | X | O | △ | X |
| Control Run 12 | X | X | X | X | X | O |

Note:
The above properties were rated as very good (◉), good (O), somewhat poor (△) or poor (X).

Thus, all of the fibroin-coated pigments produced in accordance with this invention were very good in such properties as moisture retention, adhesion to the skin, spreadability on the skin, oil absorption and feeling, and proved to be markedly excellent as compared with the blends of a fibroin powder and the uncoated carrier pigments or with the uncoated carrier pigments alone.

EXAMPLE 4

A series of fibroin solutions were prepared in the same manner as described in Example 2. However, instead of being dissolved in the calcium chloride solution, 10 parts each of the degummed spun silk waste (having a degree of crystallinity of 52%) was dissolved in 100 parts each of Schweitzer's reagent (Test Run 6), a 70% aqueous solution of lithium bromide (Test Run 7), an aqueous solution of magnesium chloride (Test Run 8), a 70% aqueous solution of calcium nitrate (Test Run 9), a 58% aqueous solution of magnesium nitrate (Test Run 10), a 50% aqueous solution of calcium thiocyanate (Test Run 11), a 50% aqueous solution of sodium thiocyanate (Test Run 12) and a 50% aqueous solution of magnesium thiocyanate (Test Run 13). These fibroin solutions were dialyzed in the same manner as described in Example 2, and the resulting aqueous fibroin solutions were adjusted to a fibroin concentration of 5.0%. While 50 parts of each of these aqueous fibroin solutions was being stirred, 10 parts of zinc oxide having a particle diameter of 0.1–10μ was added thereto and dispersed therein to form a homogeneous suspension. Then, this suspension was exposed to ultrasonic waves having a frequency of 47 kHz for 3 hours, whereby the fibroin was coagulated and precipitated on the surfaces of the zinc oxide particles. The coagulum so formed was dehydrated by centrifugation, dried, and then pulverized in the same manner as described in Example 1. Thereafter, the resulting powder was subjected to a wet heat treatment comprising exposure to saturated steam at 90° C. for 30 minutes. When the fibroin-coated pigments thus obtained were dyed in the same manner as described in Example 1, the entire surfaces of the particles were found to be brightly colored in yellow, as was the case with the fibroin-coated pigments of Examples 1 and 3. This demonstrates that, in all of the above fibroin-coated pigments, the particles of the zinc oxide used as the carrier pigment were uniformly coated with a film of regenerated fibroin.

With respect to the above fibroin-coated pigments, the amount of regenerated fibroin present on the zinc oxide particles, the hot-water-insoluble fibroin content of the regenerated fibroin, and the degree of crystallinity of the film of regenerated fibroin were determined. The results thus obtained are summarized in Table 4. In addition, they were subjected to practical performance tests for the purpose of evaluating their performance as a cosmetic preparation (e.g., face powder). The results thus obtained are summarized in Table 5.

TABLE 4

| Fibroin-coated Pigment | Amount of Regenerated Fibroin (%) | Hot-water-insoluble Fibroin Content [or Rate of β-Configuration] (%) | Degree of Crystalinity (%) |
|---|---|---|---|
| Test Run 6 | 10.1 | 85.1 | 28 |
| Test Run 7 | 10.2 | 81.6 | 29 |
| Test Run 8 | 30.4 | 90.6 | 28 |
| Test Run 9 | 10.0 | 82.5 | 30 |
| Test Run 10 | 50.4 | 95.7 | 27 |
| Test Run 11 | 25.4 | 96.1 | 29 |
| Test Run 12 | 25.3 | 97.0 | 30 |
| Test Run 13 | 25.2 | 95.4 | 30 |

TABLE 5

| Fibroin-coated Pigment | Moisture Retention | Adhesion to the Skin | Spreadability on the Skin | Oil Absorption | Feeling | Covering Power |
|---|---|---|---|---|---|---|
| Test Run 6 | ○ | ◉ | ◉ | ○ | ○ | ◉ |
| Test Run 7 | ○ | ◉ | ◉ | ○ | ○ | ◉ |
| Test Run 8 | ◉ | ◉ | ◉ | ◉ | ○ | ◉ |
| Test Run 9 | ○ | ◉ | ◉ | ◉ | ◉ | ○ |
| Test Run 10 | ◉ | ◉ | ◉ | ◉ | ◉ | ○ |
| Test Run 11 | ○ | ◉ | ◉ | ○ | ◉ | ○ |
| Test Run 12 | ○ | ◉ | ◉ | ○ | ◉ | ○ |
| Test Run 13 | ○ | ◉ | ◉ | ○ | ◉ | ○ |

Note:
The above properties were rated as very good (◉), good (○), somewhat poor (Δ) or poor (X).

EXAMPLE 5

An aqueous solution having a fibroin concentration of 5.1% was prepared in the same manner as described in Example 2. While three 100-l portions of this aqueous fibroin solution were being stirred, 20 kg each of titanium oxide having a particle diameter of 0.1 to 10μ was added thereto and dispersed therein to form homogeneous suspensions. Then, these suspensions were subjected, with stirring, to one of the following treatments:

(1) Coagulation at the isoelectric point (Test Run 14)

The suspension was adjusted to pH 4.5 (isoelectric point) by adding 0.1 N sulfuric acid thereto drop by drop, and then allowed to stand at room temperature for 10 minutes.

(2) Exposure to ultrasonic waves (Test Run 15)

A 30 kHz ultrasonic wave generator was attached to the inside wall of the vessel in which the suspension was placed, and operated at room temperature for 1 hour.

(3) Aeration (Test Run 16)

Using a pipe, air was fed at a rate of 10 l/min. and bubbled through the suspension for 10 minutes.

In every case, the suspension formed a coagulum consisting of the pigment particles coated with a gel of regenerated fibroin. This coagulum was dehydrated by means of a centrifuge and then dried in hot air at 105° C. Thereafter, the resulting product was pulverized in a jet mill until its particle diameter was reduced to 5–40μ, and then subjected to a wet heat treatment comprising exposure to saturated steam at 120° C. for 30 minutes.

With respect to the fibroin-coated pigments thus obtained, the hot-water-insoluble fibroin content (or rate of β-configuration) of the regenerated fibroin was 94.0% in case of coagulation at the isoelectric point, 99% in case of exposure to ultrasonic waves, and 85.5% in case of aeration. The degree of crystallinity as determined by X-ray diffraction analysis was 31% in case of coagulation at the isoelectric point, 33% in case of exposure to ultrasonic waves, and 42% in case of aeration. The amount of regenerated fibroin present on the pigment particles was 24.5% (based on the weight of the carrier pigment) in case of coagulation at the isoelectric point, 25.0% in case of exposure to ultrasonic waves, and 24.2% in case of aeration.

When the above fibroin-coated pigments were dyed with Tartrazine NS and then examined microscopically, the entire surfaces of the particles were found to be brightly and evenly colored in yellow. This demonstrates that, in all of these fibroin-coated pigments, the particles of the titanium oxide used as the carrier pigment were coated with a film of regenerated fibroin in a substantially uniform manner.

Then, the above fibroin-coated pigments were subjected to practical performance tests for the purpose of evaluating their performance as a cosmetic preparation. These tests were conducted in the same manner as described in Example 2. The results thus obtained are summarized in Table 6.

TABLE 6

| Type of Treatment | Moisture Retention | Adhesion to the Skin | Spreadability on the Skin | Oil Absorption | Feeling | Covering Power |
|---|---|---|---|---|---|---|
| Coagulation | ◉ | ◉ | ◉ | ◉ | ◉ | ◉ |

TABLE 6-continued

| Type of Treatment | Moisture Retention | Adhesion to the Skin | Spreadability on the Skin | Oil Absorption | Feeling | Covering Power |
|---|---|---|---|---|---|---|
| at the Isoelectric Point | | | | | | |
| Exposure to Ultrasonic Waves | ⊚ | ⊚ | ⊚ | ⊚ | ○ | ⊚ |
| Aeration | ○ | ⊚ | ⊚ | ⊚ | ○ | ⊚ |

Note:
The above properties were rated as very good (⊚), good (○), somewhat poor (Δ) or poor (X).

TABLE 7

| Fibroin-coated pigment | Moisture Retention | Adhesion to the Skin | Spreadability on the Skin | Oil Absorption | Feeling | Covering Power |
|---|---|---|---|---|---|---|
| Test Run 17 | ⊚ | ⊚ | ⊚ | ○ | ⊚ | ⊚ |
| Test Run 18 | ⊚ | ⊚ | ⊚ | ○ | ⊚ | ⊚ |

Note:
The above properties were rated as very good (⊚), good (○), somewhat poor (Δ) or poor (X).

EXAMPLE 6

A fibroin solution having a fibroin concentration of 10% was prepared in the same manner as described in Example 1, and then analyzed in the same manner as described in Example 2. Thereafter, the resulting aqueous fibroin solution (having a fibroin concentration of 5.0%) was worked up according to the procedure of Example 2. With respect to the fibroin-coated pigment (Test Run 17) thus obtained, the hot-water-insoluble fibroin content (or rate of β-configuration) of the regenerated fibroin was 84.1%, the degree of crystallinity as determined by X-ray diffraction analysis was 31%, and the amount of regenerated fibroin present on the titanium oxide particles was 25.1% based on the weight of the titanium oxide.

On the other hand, the above-described procedure was repeated except that the wet heat treatment of the pulverized product was omitted. With respect to the fibroin-coated pigment (Test Run 18) thus obtained, the hot-water-insoluble fibroin content was 54.1%, the degree of crystallinity was 23%, and the amount of regenerated fibroin was 25.1% based on the weight of the titanium oxide.

When these fibroin-coated pigments were dyed in the same manner as described in Example 1 and then examined microscopically, the entire surfaces of the particles were found to be brightly and evenly colored in yellow. This demonstrates that, in both these fibroin-coated pigments, the particles of the titanium oxide used as the carrier pigment were coated with a film of regenerated fibroin in a substantially uniform manner.

Then, the above fibroin-coated pigments were subjected to practical performance tests for the purpose of evaluating their performance as a cosmetic preparation. These tests were conducted in the same manner as described in Example 2. The results thus obtained are summarized in Table 7.

EXAMPLE 7

Spun silk waste was degummed in the same manner as described in Example 1, and the resulting powder had a degree of crystallinity of 52%. A series of fibroin solutions having the fibroin concentrations indicated in Table 8 were prepared by dissolving the degummed spun silk waste in aqueous zinc chloride solutions having the concentrations indicated in Table 8.

While the specified amount (Table 8) of each of these fibroin solutions was being stirred, 10 parts of talc (as used in Example 1) was added thereto and dispersed therein to form a homogeneous suspension. Then, this suspension was mixed with a concentrated aqueous solution containing the same amount of ammonium sulfate as that of zinc chloride present in the fibroin solution used, whereby the fibroin was coagulated (or regenerated). The coagulum so formed was heat-treated at 70° C. for 20 minutes in the same concentrated aqueous solution of ammonium sulfate, washed with water, and then dehydrated by centrifugation. When the fibroin concentration was in the range of 3–20% as taught by this invention, a homogeneous mass of gel was formed. Upon dehydration by centrifugation, this mass of gel was broken to pieces having a size of several millimeters or less. However, when the fibroin concentration was less than 3% or greater than 20% as in the Control Runs, a white precipitate was formed instead of a homogeneous mass of gel. This precipitate was so sticky that it could hardly be separated by conventional filtration under reduced pressure. Moreover, when it was placed in a cloth bag and then centrifuged, it agglomerated and cohered to form a bulky mass which was very difficult of dehydration and drying. The dehydrated mass of gel was then dried in a hot-air oven kept at 90°–100° C. or a vacuum dryer kept at 70° C. to obtain a fine granular product of fibroin-coated pigment. Subsequently, this granular product was pulverized in a jet mill to obtain a fine powder of fibroin-coated pigment consisting of nearly globular particles, 98% or more of which had a diameter of 6–30μ.

The data are summarized in Table 8.

TABLE 8

| | Zinc Chloride Concentration (%) | Fibroin Concentration (%) | Rate of β-Configuration (%) | Amount of Regenerated Fibroin (%) | Amount of Fibroin Solution Used (Parts) | Degree of Crystallinity (%) |
|---|---|---|---|---|---|---|
| Control Run 13 | 10 | 1 | 5 | 9.9 | 100 | 8 |
| Test Run 19 | 10 | 3 | 58 | 9.9 | 33 | 15 |
| Test Run 20 | 10 | 4 | 59 | 11.3 | 30 | 20 |
| Test Run 21 | 10 | 6 | 60 | 17.1 | 30 | 25 |
| Test Run 22 | 10 | 10 | 61 | 30.0 | 30 | 27 |
| Test Run 23 | 10 | 15 | 63 | 44.1 | 30 | 26 |
| Test Run 24 | 10 | 20 | 59 | 59.0 | 30 | 29 |
| Control Run 14 | 20 | 1 | 16 | 9.8 | 100 | 8 |
| Test Run 25 | 20 | 3 | 62 | 9.7 | 33 | 18 |
| Test Run 26 | 20 | 4 | 63 | 11.6 | 30 | 25 |

TABLE 8-continued

|  | Zinc Chloride Concentration (%) | Fibroin Concentration (%) | Rate of β-Configuration (%) | Amount of Regenerated Fibroin (%) | Amount of Fibroin Solution Used (Parts) | Degree of Crystallinity (%) |
|---|---|---|---|---|---|---|
| Test Run 27 | 20 | 6 | 66 | 17.8 | 30 | 29 |
| Test Run 28 | 20 | 10 | 68 | 29.9 | 30 | 28 |
| Test Run 29 | 20 | 15 | 69 | 44.5 | 30 | 27 |
| Test Run 30 | 20 | 20 | 62 | 59.0 | 30 | 20 |
| Control Run 15 | 40 | 1 | 13 | 9.8 | 100 | 7 |
| Test Run 31 | 40 | 3 | 65 | 9.9 | 33 | 20 |
| Test Run 32 | 40 | 4 | 70 | 11.9 | 30 | 25 |
| Test Run 33 | 40 | 6 | 71 | 17.6 | 30 | 30 |
| Test Run 34 | 40 | 10 | 72 | 29.8 | 30 | 29 |
| Test Run 35 | 40 | 20 | 69 | 74.0 | 37 | 27 |
| Control Run 16 | 40 | 25 | 5 | 74.5 | 30 | 8 |
| Control Run 17 | 60 | 1 | 1 | 9.8 | 100 | 5 |
| Test Run 36 | 60 | 3 | 67 | 9.8 | 33 | 18 |
| Test Run 37 | 60 | 4 | 68 | 11.5 | 30 | 25 |
| Test Run 38 | 60 | 6 | 69 | 17.5 | 30 | 29 |
| Test Run 39 | 60 | 10 | 72 | 29.5 | 30 | 28 |
| Test Run 40 | 60 | 20 | 68 | 74.0 | 37 | 29 |
| Control Run 18 | 60 | 25 | 6 | 74.3 | 30 | 8 |
| Control Run 19 | 80 | 1 | 5 | 9.8 | 100 | 5 |
| Test Run 41 | 80 | 3 | 59 | 9.9 | 33 | 19 |
| Test Run 42 | 80 | 4 | 62 | 11.5 | 30 | 23 |
| Test Run 43 | 80 | 6 | 63 | 17.5 | 30 | 25 |
| Test Run 44 | 80 | 10 | 68 | 30.0 | 30 | 27 |
| Test Run 45 | 80 | 15 | 72 | 44.5 | 30 | 27 |
| Test Run 46 | 80 | 20 | 70 | 74.0 | 37 | 29 |
| Control Run 20 | 80 | 25 | 5 | 74.4 | 30 | 8 |
| Control Run 21 | 3 | 3 | — | — | — | — |
| Control Run 22 | 90 | 10 | 43 | 29.1 | 30 | 7 |

Note:
When the zinc chloride concentration was less than 10% the degummed spun silk waste was not dissolved even after a long period of time (i.e., 24 hours or more).

EXAMPLE 8

Spun silk waste was degummed in the same manner as described in Example 1 and used as the starting material for the production of fibroin-coated pigments. A series of fibroin solutions were prepared by dissolving 10 parts of the degummed spum silk waste in 100 parts each of aqueous calcium chloride solutions having the concentrations indicated in Table 9.

Then, these fibroin solutions were desalted by passing each of them through a dialyzer of the hollow-fiber type at a rate of 1 l/hr. The dialyzer comprised 2,000 hollow fibers of regenerated cellulose having an internal diameter of 200μ, a membrane thickness of 20μ, and a length of 500 mm, both ends of these hollow fibers being bundled and sealed without blocking up their bores. In this case, the ratio of membrane surface area (cm$^2$) to priming volume (cm$^3$) had a value of 100. The resulting aqueous fibroin solutions had a fibroin concentration of 3.5–7.1% and a residual calcium chloride concentration of 0.01–0.063%.

The molecular weight of the fibroin contained in each of these aqueous fibroin solutions was determined by gel permeation chromatography. Thus, it was found that, when the calcium chloride concentration was greater than 80% as in Control Runs 32 and 33, the molecular weight was reduced to the order of 40,000.

The above aqueous fibroin solutions were adjusted, either by concentration or by dilution, to the respective fibroin concentrations indicated in Table 9. While the specified amount (Table 9) of each of the aqueous fibroin solutions was being stirred, 10 parts of talc was added thereto and dispersed therein to form a homogeneous suspension. This suspension was agitated at room temperature and at such a high speed as to give a shear rate of the order of 100/sec. Typically, in the course of 2–3 hours' agitation, the fibroin gradually precipitated and ultimately formed a mass of gel comprising an aggregation of small pieces of gel. However, when the fibroin concentration was less than 3% or greater than 20% as in the Control Runs, a white precipitate was formed instead of a homogeneous mass of gel. This precipitate was so sticky that it could hardly be separated by conventional filtration under reduced pressure. Moreover, when it was placed in a cloth bag and then centrifuged, it agglomerated and cohered to form a bulky mass which was very difficult of dehydration and drying. The above mass of gel was dehydrated by means of a centrifuge and then dried at 105° C. Thereafter, the resulting product was pulverized in a jet mill and then subjected to a wet heat treatment comprising exposure to saturated steam at 110° C. for 15 minutes. The fine powder thus obtained consisted of nearly globular particles, 98% or more of which had a diameter of 5–30μ.

The data on the amount of aqueous fibroin solution used, fibroin concentration, average molecular weight, the rate of β-configuration, and the degree of crystallinity are summarized in Table 9.

TABLE 9

| | Calcium Chloride Concentration (%) | Fibroin Concentration (%) | Amount of Aqueous Fibroin Solution Used(parts) | Average Molecular Weight (× 10⁴) | Amount of Regenerated Fibroin (%) | Rate of β-Configuration (%) | Degree of Crystallinity (%) |
|---|---|---|---|---|---|---|---|
| Control Run 23 | 10 | 1 | 100 | 10.1 | 9.7 | 27 | 8 |
| Test Run 47 | 10 | 3 | 33 | 10.1 | 9.7 | 71 | 30 |
| Test Run 48 | 10 | 4 | 30 | 10.1 | 11.4 | 79 | 31 |
| Test Run 49 | 10 | 6 | 30 | 10.1 | 17.4 | 82 | 32 |
| Test Run 50 | 10 | 10 | 30 | 10.1 | 29.2 | 84 | 33 |
| Test Run 51 | 10 | 15 | 30 | 10.1 | 44.3 | 81 | 34 |
| Test Run 52 | 10 | 20 | 37 | 10.1 | 73.5 | 79 | 34 |
| Control Run 24 | 20 | 1 | 100 | 9.7 | 9.7 | 37 | 8 |
| Test Run 53 | 20 | 3 | 33 | 9.7 | 9.7 | 75 | 31 |
| Test Run 54 | 20 | 4 | 30 | 9.7 | 11.5 | 86 | 31 |
| Test Run 55 | 20 | 6 | 30 | 9.7 | 17.2 | 90 | 32 |
| Test Run 56 | 20 | 10 | 30 | 9.7 | 29.5 | 96 | 34 |
| Test Run 57 | 20 | 20 | 37 | 9.7 | 73.6 | 93 | 32 |
| Test Run 58 | 20 | 20 | 30 | 9.7 | 74.3 | 20.5 | 7 |
| Control Run 25 | 40 | 1 | 100 | 8.6 | 9.8 | 40 | 8 |
| Test Run 59 | 40 | 3 | 33 | 8.6 | 9.8 | 79 | 31 |
| Test Run 60 | 40 | 4 | 30 | 8.6 | 11.6 | 83 | 33 |
| Test Run 61 | 40 | 6 | 30 | 8.6 | 17.8 | 93 | 33 |
| Test Run 62 | 40 | 10 | 30 | 8.6 | 29.5 | 98 | 34 |
| Test Run 63 | 40 | 20 | 37 | 8.6 | 73.8 | 94 | 32 |
| Control Run 26 | 40 | 25 | 30 | 8.6 | 74.8 | 23 | 8 |
| Control Run 27 | 60 | 1 | 100 | 8.5 | 9.8 | 42 | 9 |
| Test Run 64 | 60 | 3 | 33 | 8.5 | 9.8 | 80 | 30 |
| Test Run 65 | 60 | 4 | 30 | 8.5 | 11.8 | 83 | 32 |
| Test Run 66 | 60 | 6 | 30 | 8.5 | 17.8 | 92 | 33 |
| Test Run 67 | 60 | 10 | 30 | 8.5 | 29.6 | 95 | 33 |
| Test Run 68 | 60 | 20 | 37 | 8.5 | 73.5 | 93 | 31 |
| Control Run 28 | 60 | 25 | 30 | 8.5 | 74.8 | 26.8 | 7 |
| Control Run 29 | 80 | 1 | 100 | 8.4 | 9.7 | 37 | 8 |
| Test Run 69 | 80 | 3 | 33 | 8.4 | 9.7 | 71 | 30 |
| Test Run 70 | 80 | 4 | 30 | 8.4 | 11.5 | 79 | 31 |
| Test Run 71 | 80 | 6 | 30 | 8.4 | 17.2 | 81 | 32 |
| Test Run 72 | 80 | 10 | 30 | 8.4 | 29.3 | 83 | 33 |
| Test Run 73 | 80 | 15 | 30 | 8.4 | 44.2 | 85 | 33 |
| Test Run 74 | 80 | 20 | 37 | 8.4 | 63.5 | 79 | 32 |
| Control Run 30 | 80 | 25 | 30 | 8.4 | 74.1 | 35 | 7 |
| Control Run 31 | 3 | — | — | — | — | — | — |
| Control Run 32 | 90 | 1 | 100 | 4.2 | 9.6 | 39 | 8 |
| Control Run 33 | 90 | 25 | 30 | 4.2 | 74.1 | 36 | 8 |

Note:
In Control 31, the degummed spun silk waste was not dissolved.

EXAMPLE 9

The fibroin-coated pigments obtained in Examples 7 and 8 were subjected to practical performance tests for the purpose of evaluating their performance as a cosmetic preparation. These tests were conducted in the same manner as described in Example 1.

Thus, it was found that the fibroin-coated pigments of Test Runs 19, 24, 25, 30, 31, 35, 36, 40 and 41 (Group 1) had nearly as good performance as the product of Test Run 1 in Example 1. Moreover, the fibroin-coated pigments of Test Runs 20-23, 26-29, 32-34, 37-39, 47 and 74 (Group 2) were better in adhesion to the skin, spreadability on the skin, and the like than those of the aforesaid Group 1. Furthermore, the fibroin-coated pigments of Test Runs 48-73 (Group 3) had as good performance as the product of Test Run 2 in Example 2, and were still better than the fibroin-coated pigments of the aforesaid Group 2.

On the other hand, the fibroin-coated pigments of Control Runs 13-20 and 23-33 were good (O) in moisture retention and covering power, but somewhat poor (Δ) in adhesion to the skin, spreadability on the skin, and feeling. Thus, they were inferior in performance to the fibroin-coated pigments of the aforesaid Groups 1-3. Moreover, the fibroin-coated pigments of these Control Runs had the disadvantage that, whether they are used alone or in combination with untreated pigments, they cohered or agglomerated under the influence of water, formed secondary particles, and gave a sticky feeling.

EXAMPLE 10

A mixture of 20 parts of liquid paraffin, 5 parts of ceresin, 5 parts of lanolin, 10 parts of microcrystalline wax, and 31.2 parts of isopropyl myristate was melted, with stirring, by heating it to 90° C. To the resulting melt was added 32 parts of a pigment. This mixture was kneaded well, poured into a mold, and then cooled. The oil-base foundation thus obtained was allowed to stand at a relative humidity of 90% and a temperature of 40° C., and then observed visually to examine the presence or absence of oil droplet formation on its surface.

Thus, it was found that, when the pigment consisted of 40 parts of a fibroin-coated pigment selected from the products of Test Runs 1-74 or 31 parts of the fibroin-coated pigment mixed with 0.3 part of red iron oxide and 0.7 part of yellow iron oxide, no oil droplet formation was noted. Moreover, the uniformity of dispersion of the pigment was satisfactorily good.

On the other hand, when the pigment consisted of 40 parts of a fibroin-coated pigment selected from the products of Control Runs 13-35 or 31 parts of the fibroin-coated pigment mixed with 0.3 part of red iron oxide and 0.7 part of yellow iron oxide, a considerable degree of oil droplet formation was noted, and the uniformity of dispersion of the pigment was relatively poor.

Furthermore, when the pigment consisted of 40 parts of titanium oxide or talc or 31 parts of titanium oxide or talc mixed with 0.3 part of red iron oxide and 0.7 part of yellow iron oxide, a considerable degree of oil droplet formation was also noted, and the uniformity of dispersion of the pigment was significantly poorer than in the oil-base foundations made in accordance with this invention.

EXAMPLE 11

With respect to the fibroin-coated pigments of Test Runs 2 and 14–18 and untreated titanium oxide, the measurement of oil absorption was made according to the milling method described in JIS-K5101. Thus, it was found that the oil absorption was 55.6% for the product of Test Run 2, 58.9% for the products of Test Runs 14 and 15, 57.5% for the product of Test Run 16, 57.1% for the product of Test Run 17, and 53% for the product of Test Run 18. On the other hand, the oil absorption of untreated titanium oxide was 36.1%.

COMPARATIVE EXAMPLE 1

The procedure described in Example 4 of Japanese Patent Publication No. 299/'52 was repeated except that the aqueous fibroin solution of Test Run 62 (having a fibroin concentration of 10%) or that of Test Run 63 (having a fibroin concentration of 20%) was used as the colloidal solution of fibroin, and the coloring matter and perfume were omitted. More specifically, a pigment was thoroughly mixed with either of the aqueous fibroin solutions, and the resulting mixture was dried at 70° C.

With respect to the treated pigments thus obtained, the amount of regenerated fibroin present on the pigment particles were 0.36% for the former and 0.72% for the latter. The hot-water-insoluble fibroin content (or rate of $\beta$-configuration) of the regenerated fibroin was 0% for either of them, indicating that all (100%) of the regenerated fibroin was constituted of that type of fibroin having $\beta$-configuration. In consequence, when these treated pigments were dyed with a 2% aqueous solution of Tartrazine NS at 100° C. for 10 minutes, all of the regenerated fibroin was dissolved in the dye bath.

In addition, the above treated pigments were dyed with Shirlastain A at 40° C. for 20 minutes and then examined under an optical microscope. Thus, it was found that the fibroin was only partially deposited on the surfaces of the pigment particles and, therefore, they were not substantially coated with a film of regenerated fibroin.

Then, with respect to the above treated pigments, the measurement of oil absorption was made in the same manner as described in Example 11. Thus, the oil absorption was found to be 37.9% for the former and 39.9% for the latter. Moreover, when evaluated in the same manner as described in Example 10, these treated pigments showed no ability to prevent the formation of oil droplets and fairly poor dispersibility in oil. Furthermore, in order to evaluate their performance as a cosmetic preparation, these treated pigments were tested in the same manner as described in Example 1. Thus, they were found to be somewhat poor ($\Delta$) in moisture retention, adhesion to the skin, spreadability on the skin, and feeling. Although their covering power was rated as good ($\bigcirc$), it showed no improvement and seemed to be significantly poorer than that of the fibroin-coated pigments of Test Runs 1–74.

What is claimed is:

1. A fibroin-coated pigment comprising a carrier pigment in the form of finely divided particles whose surfaces are substantially coated with a film of regenerated fibroin, the regenerated fibroin having a degree of crystallinity of at least 10%, the amount of the regenerated fibroin being in the range of 2 to 100% by weight based on the weight of the carrier pigment, at least 50% by weight of the regenerated fibroin being constituted of hot-water-insoluble fibroin having the $\beta$-configuration.

2. A fibroin-coated pigment as claimed in claim 1 wherein from 80 to 100% by weight of the regenerated fibroin is constituted of hot-water-insoluble fibroin having the $\beta$-configuration.

3. A fibroin-coated pigment as claimed in claim 1 wherein the film of regenerated fibroin has a degree of crystallinity of from 20 to 43%.

4. A fibroin-coated pigment as claimed in claim 1 wherein the film of regenerated fibroin is present in an amount of from 5 to 50% by weight based on the weight of the carrier pigment.

5. A fibroin-coated pigment as claimed in claim 1 wherein the regenerated fibroin has an average molecular weight of at least 50,000.

6. A fibroin-coated pigment as claimed in claim 1 which has a maximum particle diameter of from 0.05 to 100$\mu$.

7. A fibroin-coated pigment as claimed in claim 1 wherein the carrier pigment is selected from the group consisting of talc, kaolin, mica, calcium carbonate, titanium oxide, zinc oxide, micaceous titanium, magnesium carbonate, iron oxides, zinc stearate, magnesium stearate, magnesium silicate, organic pigments and combinations thereof.

8. A process for producing a fibroin-coated pigment which comprises the steps of dissolving a degummed silk material in at least one solvent selected from the group consisting of an aqueous cupri-ethylenediamine solution, an aqueous ammoniacal solution of cupric hydroxide, an aqueous alkaline solution of cupric hydroxide and glycerol, an aqueous lithium bromide solution and an aqueous solution of the chloride or nitrate of calcium, magnesium or zinc; dispersing a carrier pigment in the resulting fibroin solution having a fibroin concentration of from 3 to 20% by weight; adding a coagulating salt to the pigment-loaded fibroin solution to coagulate and precipitate the fibroin; dehydrating and drying the resulting coagulum; and then pulverizing the dried product.

9. A process for producing a fibroin-coated pigment which comprises the steps of dissolving a degummed silk material in at least one solvent selected from the group consisting of an aqueous cupri-ethylenediamine solution, an aqueous ammoniacal solution of cupric hydroxide, an aqueous alkaline solution of cupric hydroxide and glycerol, an aqueous lithium bromide solution and an aqueous solution of the chloride or nitrate of calcium, magnesium or zinc, and an dialyzing the resulting fibroin solution; dispersing a carrier pigment in the resulting aqueous fibroin solution having a fibroin concentration of from 3 to 20% by weight; subjecting the pigment-loaded aqueous fibroin solution to at least one treatment for coagulating and precipitating the fibroin, the treatment being selected from the group consisting of the addition of a coagulating said, aeration, exposure to ultrasonic waves, and agitation at high shear rate; dehydrating and drying the resulting coagulum; and then pulverizing the dried product.

10. A process as claimed in claim 8 wherein the fibroin solution has a fibroin concentration of from 4 to 15% by weight.

11. A process as claimed in claim 9 wherein the aqueous fibroin solution has a fibroin concentration of from 4 to 15% by weight.

12. A process as claimed in claim 8 wherein the fibroin solution is used in an amount of at least 100% by weight based on the weight of the carrier pigment.

13. A process as claimed in claim 9 wherein the aqueous fibroin solution is used in an amount of at least 100% by weight based on the weight of the carrier pigment.

14. A process as claimed in claim 8 or 9 wherein the coagulating salt is selected from the group consisting of ammonium sulfate, sodium sulfate, sodium chloride and combinations thereof.

15. A process as claimed in claim 8 or 9 wherein the coagulating salt is used in an amount of from 2 to 10% by weight based on the weight of the water present in the coagulation system.

16. A process as claimed in claim 9 wherein the aeration is carried out by bubbling air through the pigment-loaded aqueous fibroin solution for a period of 1 hour or more, the air being fed at a rate of at least 0.1 l/min. for each liter of the pigment-loaded aqueous fibroin solution.

17. A process as claimed in claim 9 wherein the exposure to ultrasonic waves is carried out by generating ultrasonic waves having a frequency of 30 kHz or higher and exposing the pigment-loaded aqueous fibroin solution to these ultrasonic waves for a period of 1 hour or more.

18. A process as claimed in claim 9 wherein the agitation at high shear rate is carried out at a shear rate of 50/sec or more.

19. A process as claimed in claim 9 wherein the product resulting from the drying or pulverizing step is heat-treated with saturated steam at a temperature of 50° C. or above.

20. A process as claimed in claim 8 or 9 wherein, prior to the drying step, the coagulum is heat-treated in an aqueous solution of ammonium sulfate, sodium sulfate or potassium sulfate at a temperature of 50° C. or above.

21. A fibroin-coated pigment consisting essentially of finely divided carrier pigment particles each coated with a substantially uniform coating film of regenerated fibroin having an average molecular weight of 80,000 to 150,000, said carrier pigment particles having a maximum particle size of from 0.03 to 100$\mu$, the amount of said regenerated fibroin being in the range of 5 to 50% by weight based on the weight of said carrier pigment particles and the thickness of said film of regenerated fibroin being in the range of from 0.01 to 50$\mu$, said regenerated fibroin having a degree of crystallinity of from 20 to 43% and at least 80% by weight of said regenerated fibroin consisting of hot-water-insoluble fibroin having the $\beta$-configuration.

* * * * *

UNITED STATES PATENT AND TRADEMARK OFFICE
CERTIFICATE OF CORRECTION

PATENT NO. : 4 325 741

DATED : April 20, 1982

INVENTOR(S) : Kiyoshi Otoi et al

It is certified that error appears in the above—identified patent and that said Letters Patent is hereby corrected as shown below:

Column 24, line 61; change "zinc, and an dialyzing" to ---zinc; dialyzing---.

Column 24, line 68; change "said" to ---salt---.

Signed and Sealed this

Seventeenth Day of August 1982

[SEAL]

Attest:

GERALD J. MOSSINGHOFF

Attesting Officer     Commissioner of Patents and Trademarks